United States Patent [19]
Horodysky

[11] Patent Number: 4,587,026
[45] Date of Patent: May 6, 1986

[54] MULTIFUNCTIONAL LUBRICANT ADDITIVES

[75] Inventor: Andrew G. Horodysky, Cherry Hill, N.J.

[73] Assignee: Mobil Oil Corporation, New York, N.Y.

[21] Appl. No.: 622,820

[22] Filed: Jun. 21, 1984

[51] Int. Cl.$^4$ ................ C10M 149/00; C10M 151/00; C10M 153/00
[52] U.S. Cl. .................................. 252/47.5; 252/46.3; 252/49.6; 558/289; 558/292
[58] Field of Search .................... 252/46.3, 47.5, 49.6; 260/462 R

[56] References Cited

U.S. PATENT DOCUMENTS

| | | | |
|---|---|---|---|
| 1,888,023 | 11/1932 | Adams | 252/51.5 R |
| 1,973,676 | 9/1934 | Voorhees | 252/50 |
| 2,189,788 | 2/1940 | Freeman | 252/51.5 R |
| 2,234,096 | 3/1941 | Teter et al. | 252/50 |

Primary Examiner—William R. Dixon, Jr.
Assistant Examiner—Cynthia A. Prezlock
Attorney, Agent, or Firm—Alexander J. McKillop; Michael G. Gilman; Howard M. Flournoy

[57] ABSTRACT

Amine-sulfurized hydrocarbyl or hydrocarbyloxy phenol borates and alkoxylated derivatives thereof provide friction reducing and high temperature stabilizing properties to lubricating oils and greases into which they have been incorporated.

24 Claims, No Drawings

MULTIFUNCTIONAL LUBRICANT ADDITIVES

BACKGROUND OF THE INVENTION

This invention relates to lubricant compositions and more particularly to lubricant compositions comprising oils of lubricating viscosity or greases thereof containing a minor multifunctional amount of an amine-sulfurized alkylphenol borate or an alkoxylated amine-sulfurized alkylphenol borate or mixtures thereof. The incorporation of the amine moiety provides good friction activity and possibly antirust characteristics; the sulfurized phenol group provides antiwear and antioxidant properties; and the boron ester groups provide high temperature stabilizing characteristics.

Borated amines, borated alkanolamines, borated ureas, amine salts of boron acids, chlorinated amine-boron complexes and aromatic amine-boron compounds are known in the prior art and described respectively in U.S. Pat. Nos. 3,449,362; 3,254,025; 2,999,074; 4,226,734; 3,076,835; 4,025,445; 3,014,870; 3,014,869; 3,007,873 and borated adducts of alkylamines and alkyldiamines are disclosed as friction reducing lubricant additives in U.S. Pat. No. 4,328,113.

The borates described in this application, however, provide in a single lubricant additive composition substantial antiwear, corrosion inhibiting, friction reducing, and high temperature stabilizing properties. These new compositions combine the beneficial properties imparted by sulfur, phenol and amine or alkoxylated amine and borate moieties within a single composition to provide a full range of benefits previously unavailable in a single additive compound. The additives compositions per se, as well as the lubricant or fuel compositions made therefrom are thus believed to be novel and unique. Accordingly, to the best of applicant's knowledge, these compositions have not been previously known or used as multifunctional-friction reducing additives in lubricant applications.

SUMMARY OF THE INVENTION

This invention is more particularly directed to amine-sulfurized hydrocarbyl phenol borates and alkoxylated amine-sulfurized hydrocarbyl phenol borates. Hydrocarbyl includes alkyl, alkylene, cycloalkyl, aryl and alkaryl. Suitable amines include diamines, and corresponding hydrocarbyl hydrocarbylene and hydrocarbyloxy hydrocarbylene diamines and primary, secondary and tertiary amines and corresponding hydrocarbyl and hydrocarbyloxy hydrocarbylene amines which generally have from about 8 to 29 carbon atoms.

The invention is also directed to lubricant compositions having reduced friction, high temperature stabilization and reduced bearing corrosion containing such amine and such alkoxylated amine borated derivatives or mixtures thereof and to a method of reducing fuel consumption in internal combustion engines comprising treating the moving surfaces of the engine with said lubricant compositions.

DESCRIPTION OF PREFERRED EMBODIMENTS

Any of several groups of hydrocarbyl amines, hydrocarbyl diamines or alkoxylated hydrocarbyl amines or alkoxylated hydrocarbyl diamines have been found to be useful in this invention. Suitable amines include, but are not limited to, t-alkylamines, oleylamine, tallowamine, hydrogenated tallowamine, soyamine, and cocoamine. Suitable diamines include, but are not limited to N-oleyl-1,3-propylenediamine, N-tallow-1,3-propylenediamine, N-coco-1,3-propylenediamine, N-soya-1,3-propylenediamine as well as the corresponding N-hydrocarbyl ethylenediamines. Included in the diamine category are the N-hydrocarbyloxy hydrocarbylene diamines, such as N-triisodecyloxypropyl-1,3-propylenediamine and the like.

The alkoxylated amines and diamines include ethoxylated, polyethoxylated, propoxylated and polypropoxylated derivatives of each of the above groups of amines including, but not limited to mono- or polyethoxylated or mono- or polypropoxylated etheramines, hydroxyethyl oleylamine, hydroxyethyl tallowamine, hydroxyethyl cocoamine, hydroxypropyl oleylamine, hydroxypropyl soyamine, hydroxypropyl cocoamine, bis(2-hydroxyethyl)oleylamine, bis(2-hydroxyethyl)soyamine, bis(2-hydroxyethyl)cocoamine, bis(2-hydroxyethyl)oleylamine, bis(2-hydroxypropyl)tallowamine, polyethoxylated oleylamine, polyethoxylated tallowamine, polypropoxylated tallowamine, polypropoxylated cocoamine, ethoxylated N-oleyl-1,3-propylenediamine, ethoxylated N-tallow-1,3-propylenediamine, propoxylated N-oleyl-1,3-propylenediamine, propoxylated N-tallow-1,3-propylenediamine, alkoxylated N-hydrocarbylethylenediamines and alkoxylated N-hydrocarbyloxy hydrocarbylene diamines.

The amines can be represented by:

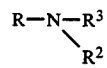

where $R=C_6$ to $C_{30}$ hydrocarbyl or hydrocarbyloxy, $R^2$ and $R^3$ each separately=H, $(R^1)_xH$, R or

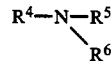

$R^1=C_2$ or $C_3$ hydrocarbyloxy, $R^4=C_2$ or $C_3$ hydrocarbyl, $R^5$ and $R^6$ are each separately H or $(R^1)_xH$, where x is from 1 to about 10.

Several different groups of phenols can be used. Preferred are sulfurized phenols made by the direct sulfurization of hydrocarbyl phenols, or by reaction with a sulfur halide such as sulfur dichloride or sulfur monochloride. Hydrocarbyl phenols such as butyl phenol, nonyl phenol and dodecyl phenol are preferably used for the sulfurization reaction product which is described below:

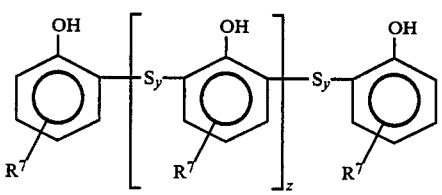

$R^7$ is $C_3-C_{30}$ hydrocarbyl, y is 1 through 4 and z is 0 through 4.

The boration can be performed using boric acid, trihydrocarbyl borates such as tributyl borate or any other similar or convenient borating agent. A stoichiometric amount of boronating agent can be used or an excess of boronating agent of up to a 50-100% excess or more can be used and is often desirable for certain applications such as solid lubricants. Thus, boration can be complete or partial. Usually boration levels vary from about 0.05 to about 7 weight %.

Preferably the borated derivatives are prepared in the presence of an alcoholic or hydrocarbon solvent. The presence of a solvent is not essential, however. If one is used, it may be reactive or non-reactive. Suitable non-reactive solvents include benzene, toluene, xylene and the like. Suitable reactive solvents include isopropanol, butanol, the pentanols and the like. Reaction temperatures may vary from about 70° to about 250° C. with about 110° to about 170° C. being preferred.

The amine sulfurized products can be described by simple formulas but are believed to be complex mixtures. As a generalization, however, structures which can be present include those represented by:

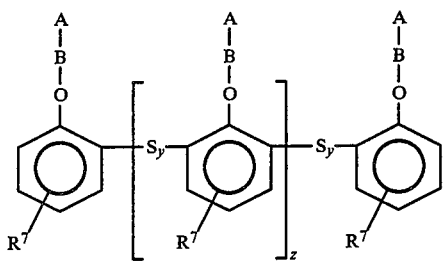

where $R^7$ as described above = hydrogen or $C_3-C_{30}$ hydrocarbyl, preferably $C_6-C_{20}$ hydrocarbyl and $Y=1$ to 4, $Z=0$ to 4 and A is one or more amine structures described above such as:

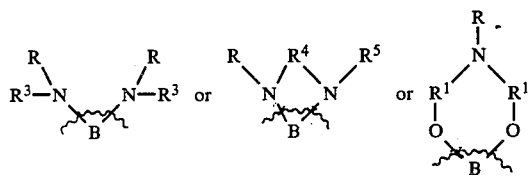

wherein R, $R^1$, $R^3$ and $R^4$ are as described above.

The lubricant compositions contemplated for use herein comprise a major proportion of an oil of lubricating viscosity or grease prepared therefrom and include both mineral and synthetic hydrocarbon oils of lubricating viscosity, mixtures of mineral and synthetic oils and greases prepared therefrom which contain a minor effective proportion of a multifunctional friction reducing additive consisting of a hydrocarbyl amine or diamine, a hydrocarbyloxy hydrocarbylene amine or diamine, a hydrocarbyl alkoxylated amine or diamine, a hydrocarbyloxy hydrocarbylene alkoxylated amine or diamine sulfurized phenol borate and mixtures thereof wherein hydrocarbyl comprises a member selected from the group consisting of alkyl, alkanol, alkylene, cycloalkyl and alkoxy and mixtures thereof. As little as 0.28% of the borated products can reduce friction of a fully blended automotive engine oil by as much as 50% or more compared to non-borated additives. The amount of the borated product used generally varies from 0.1 to about 10 wt.%, preferably from about 2 to about 4 wt.%.

Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, especially lithium hydroxyl-carboxylate soap greases, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however in all other respects, any material which is normally employed for thickening or gelling hydrocarbon fluids for forming grease can be used in preparing the aforementioned improved grease in accordance with the present invention.

Typical synthetic oils are: polypropylene, polypropylene glycol, trimethylol propane esters, neopentyl and pentaerythritol esters, di(2-ethyl hexyl)sebacate, di(2-ethyl hexyl)adipatate, dibutyl phthalate, polyethylene glycol di(2-ethyl hexanoate), fluorocarbons, perfluoro-alkylpolyethers, silicate esters, silanes, esters of phosphorus-containing acids, liquid ureas, ferrocene derivatives, hydrogenated mineral oils, chain type polyphenyls, siloxanes, polysiloxanes, silicones, fluorosilicones, alkyl-substituted diphenyl ethers typified by a butyl-substituted bis-(p-phenoxy phenyl)ether and phenoxy phenyl ethers. Other hydrocarbon oils include synthetic hydrocarbon polymers having improved viscosity indices, which polymers are prepared by polymerizing an olefin, or mixtures of olefins, having from 5 to 10–18 carbon atoms per molecule in the presence of an aliphatic halide and a Ziegler-type catalyst.

Other additives that may be useful for their known purposes in lubricants with the product of this invention include, for example, polymeric dispersants, calcium or magnesium sulfonates or phenates, metallic dithiophosphate, polymeric VI improvers and the like.

Generally speaking the subject reactants can be obtained from standard commercial sources or they may be prepared and borated by any of a number of conventional methods known in the art.

Having described the invention in general terms, the following are offered to specifically illustrate it. It is to be understood they are illustrations only and that the invention is not thereby limited except as by the appended claims.

The following examples are typical of the additive compounds useful herein and their test data serve to demonstrate their effectiveness in lubricant compositions for reducing friction, stabilizing the compositions against oxidation, reducing bearing corrosion and conserving fuel.

Molar ratios of amine moiety to phenol sulfide that can be used range from 10:1 to 1:10 but generally preferably from 5:1 to 1:5.

EXAMPLE 1

Bis(2-hydroxyethyl)Cocamine-Dodecylphenol Sulfide Borate

Approximately 315 g of bis(2-hydroxyethyl)cocamine (commercially obtained), 50 g boric acid, 80 g toluene and 8 g butanol were placed in a reactor equipped with heater, agitator, Dean-Stark tube with condenser, and provision for blanketing vapor space with nitrogen. The reactants were heated up to 150° C. over a period of six hours until water evolution stopped. A total of 38 g water were collected. The solvent was removed by distillation at reduced pressure and the intermediate was filtered through diatomaceous earth.

Approximately 80 g of the above borated bis(2-hydroxyethyl)cocamine, 67 g of 50% dodecylphenol sulfide (made by reacting 3 moles of dodecylphenol with 2 moles of sulfur dichloride at 100° C. to 150° C. for six hours with agitation followed by vacuum topping to remove residual HCl), in 100″ solvent paraffinic neutral lubricating diluent oil, and 100 g toluene were charged to a reactor equipped as described above. The reactants were heated up to 175° C. over a period of four hours until water evolution ceased. The solvent was removed by distillation at 175° C. under reduced pressure.

EXAMPLE 2

Bis(2-Hydroxylethyl)Oleylamine-Dodecylphenol Sulfide Borate

Approximately 3150 g of bis(2-hydroxyethyl)oleylamine (obtained commercially), 200 g toluene, 30 g butanol and 750 g boric acid were charged to a reactor requipped as described in Example 1. The reactants were heated up to 170° C. over a period of ten hours until water evolution ceased. The solvents were removed by distillation at 170° C. at reduced pressure, and the intermediate was filtered through diatomaceous earth.

Approximately 100 g of the above borated bis(2-hydroxyethyl)oleylamine, 67 g of dodecylphenol sulfide oil concentrate (as described in Example 1), and 100 g toluene were charged to a reactor equipped as described above. The reactor contents were heated up to 175° C. over a period of five hours until water evolution ceased. The solvent was removed by vacuum topping at 175° C.

EXAMPLE 3

Bis(2-Hydroxyethyl)Oleylamine-Dodecylphenol Sulfide Borate

Approximately 3150 g of bis(2-hydroxyethyl)oleylamine (obtained commercially), 300 g toluene, and 543 g boric acid were charged to a reactor equipped as described in Example 1. The reactants were heated up to 160° C. over a period of fourteen hours until water evolution ceased. The solvent was removed by distillation under reduced pressure.

Approximately 180 g of the above borated bis(2-hydroxyethyl)oleylamine, 75 g toluene and 150 g of dodecylphenol sulfide oil concentrate (as described in Example 1) were charged to a reactor equipped as described above. The reactor contents were heated up to 195° C. and held for a period of four hours. The solvent was removed by distillation under reduced pressure. An additional 165 g of 100″ solvent paraffinic neutral lubricating oil was added as a diluent.

EXAMPLE 4

Bis(2-Hydroxypropyl)Cocamine-Dodeylphenol Sulfide Borate

Approximately 160 g of bis(2-hydroxypropyl)cocamine, 135 g of dodecylphenol sulfide oil concentrate (as described in Example 1), 100 g toluene and 30 g boric acid were charged to a reactor equipped as described in Example 1. The reactor contents were heated up to 175° C. over a period of six hours until water evolution during azeotropic distillation ceased. The solvent was removed by distillation at 175° C. under reduced pressure. The crude product was filtered hot through diatomaceous earth.

EXAMPLE 5

N-Oleyl-1,3-Propylenediamine-Dodecylphenol Sulfide Borate

Approximately 90 g N-oleyl-1,3-propylenediamine (commercially obtained), 100 g toluene, 135 g of dodecylphenol sulfide oil concentrate (as described in Example 1), and 20 g boric acid were charged to a reactor equipped as described in Example 1. The reactor contents were heated up to 170° C. over a period of ~five hours until water evolution during azeotropic distillation ceased. The solvent was removed by distillation under reduced pressure. The crude product was filtered hot through diatomaceous earth.

EXAMPLE 6

Oleylamine-Dodecylphenol Sulfide Borate

Approximately 78 g of oleylamine, 100 g toluene, 150 g of dodecylphenol sulfide oil concentrate (as described in Example 1), and 17 g boric acid were charged to a reactor equipped as described in Example 1. The reactor contents were heated up to 170° C. over a period of six hours until water evolution during azeotropic distillation ceased. The solvent was removed by distillation under reduced pressure and the product was filtered hot through diatomaceous earth.

The products were evaluated for friction reducing properties using the Low Velocity Friction Apparatus Test (LVFA). As shown in Tables 1 and 2, the mixed borated amine phenol sulfides exhibit unexpected frction reducing properties, considering the antioxidant, and antiwear characteristics.

Several blends comprising a minor amount (2 to 5 weight %) of several examples and the base lubricant as described below were then evaluated using the Low Velocity Friction Apparatus.

EVALUATION OF PRODUCTS

Low Velocity Friction Apparatus

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measued as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12-13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed.

Freshly polished steel specimens are used for each run. The surface of the steel is parallel ground to 4-8 microinches.

The data obtained are shown in Tables 1 and 2. The percentages by weight are percentages by weight of the total lubricating oil composition, including the usual additive package. The data are percent decrease in friction according to:

$$\frac{(U_k \text{ of oil alone}) - (U_k \text{ of additive plus oil})}{(U_k \text{ of oil alone})} \times 100$$

The value for the oil alone would be zero for the form of the data shown in Tables 1 and 2 below.

TABLE 1

Evaluation of Friction Reducing Characteristics Using low Velocity Friction Apparatus

| | Additive Conc. in Base Fluid Weight % | % Reduction in Coefficient of Friction at 5 Ft/Min | % Reduction in Coefficient of Friction at 30 Ft/Min |
|---|---|---|---|
| Test Oil (SAE 5W-30 fully formulated synthetic automotive engine oil with detergent/dispersant/inhibitor package) | — | 0 | 0 |
| Example 1 - Bis(2-hydroxyethyl) cocoamine-dodecylphenol sulfide borate concentrate in oil | 4<br>2 | 52<br>30 | 39<br>27 |
| Example 3 - Bis(2-hydroxyyethyl) oleylamine-dodecylphenol sulfide borate concentrate in oil | 2 | 24 | 17 |
| Example 4 - Bis(2-hydroxypropyl) cocamine-dodecylphenol sulfide bozate concentrate in oil | 4 | 30 | 21 |
| Example 5 - N—Oleyl-1,3-propylene-diamine-dodecylophenol sulfide borate concentrate in oil | 4 | 25 | 26 |
| Example 6 - Oleylamine-dodecylphenol sulfide borate concentrate in oil | 4 | 28 | 17 |

TABLE 2

Evaluation of Friction Characteristics Using Low Velocity Friction Apparatus

| | Additive Conc. in Base Fluid Weight % | % Reduction in Coefficient of Friction at 5 Ft/Min | % Reduction in Coefficient of Friction at 30 Ft/min |
|---|---|---|---|
| Test Oil (SAE 10W-40 fully formulated automotive engine oil with detergent/dispersant inhibitor package) | — | 0 | 0 |
| Example 1 - Bis(2-hydroxyethyl) cocoamine-dodecylphenol sulfide borate concentrate in oil | 4 | 30 | 20 |
| Example 2 - Bis(2-hydroxyethyl) oleylamine-dodecylphenol sulfide borate concentrate in oil | 4<br>2 | 37<br>31 | 25<br>25 |
| Example 4 - Bis(2-hydroxypropyl) cocamine-dodecylphenol sulfide borate concentrate in oil | 4 | 26 | 31 |
| Example 5 - N—Oleyl-1,3-propylene-diamine dodecylphenol sulfide borate concentrate in oil | 4 | 25 | 25 |

The products were also evaluated for high temperature and oxidative stability. In most cases, improvements in oxidative stability were observed. Basically, the test lubricant is subjected to a stream of air which is bubbled through the test lubricant at a rate of 5 l per hour at 325° F. for forty hours. Present in the composition are samples of metals commonly used in engine construction, namely iron, copper, aluminum and lead. See U.S. Pat. No. 3,682,980 for further details of the test. Improvement in percent viscosity increase, control of acidity and/or control of lead loss show effective control. As shown by the results of Table 3, excellent antioxidant properties are exhibited by the compositions in accordance with the invention.

TABLE 3

CATALYTIC OXIDATION TEST

| | Conc.* Wt. % | % Incr. In Viscosity of Used Oil vs. New Oil at 100° C. kv | Acid No. | Pb Loss, mg |
|---|---|---|---|---|
| Base Oil 200" Solvent Paraffinic Neutral Mineral Lubricating oil | — | 27 | 2.21 | 0.4 |
| Example 1 - Bis(2-hydroxyethyl) cocoamine-dodecylphenol sulfide borate concentrate in oil | 1 | 14 | — | — |
| Example 2 - Bis(2-hydroxyethyl) oleylamine-dodecylphenol sulfide borate concentrate in oil | 1 | 14 | — | 0.5 |
| Example 3 - Bis(2-hydroxyethyl) oleylamine-dodecylphenol sulfide borate concentrate in oil | 3<br>1 | 16<br>12 | 1.49<br>1.13 | 0.3<br>0.0 |
| Example 5 - N—Oleyl-1,3-propylene-diamine-dodecylphenol sulfide borate concentrate in oil | 1 | 15 | — | 0.6 |
| Example 6 - Oleylamine-dodecyl-phenol sulfide borate concentrate in oil | 1 | 17 | — | 0.4 |

*Examples contain diluent oil

The products' propensity to corrode copper (due primarily to the contained sulfur groups) were measured in lubricants using the ASTM D-130-80 Copper Strip Corrosivity Test at two different, but severe conditions of time and temperature. As can be seen from the data of Table 4, the products of the examples are surprisingly non-corrosive to copper.

TABLE 4
COPPER STRIP CORROSIVITY

| | Conc. in 200″ SPN Test Oil,* Wt. % | ASTM D130-80 3 Hrs. @ 250° F. | ASTM D130-80 6 Hrs. @ 212° F. |
|---|---|---|---|
| Example 1 - Bis(2-hyroxyethyl) cocoamine-doecylphenol sulfide borate concentrate in oil | 1 | 1A | 1A |
| Example 2 - Bis(2-hydroxyetyl) oleylamine-dodecylphenol sulfide borate concentrate in oil | 1 | — | 1A |
| Example 3 - Bis(2-hydroxyethyl) oleylamine-dodecylphenol sulfide borate concentrate in oil | 3<br>1 | 1A<br>1A | 1A<br>1A |
| Example 4 - Bis(2-hydroxypropyl) cocamine-dodecylphenol sulfide borate concentrate in oil | 1 | 1A | — |
| Example 5 - N—Oleyl-1,3-propylene-diamine-dodecylphenol sulfide borate concentrate in oil | 1 | 1A | 1A |
| Example 6 - Oleylamine-dodecylphenol sulfide borate concentrate in oil | 1 | 1A | 1A |

*Examples contain diluent oil

Amine, alkoxylated amine, and diamine-sulfurized phenol borates in accordance with this invention exhibit good friction reducing properties (50% or greater reduction in the coefficients of friction), high temperature stabilizing, antiwear and antioxidant characteristics when formulated at low additive concentrations into lubricating fluids and greases. These mixed borates are derived in part, from amines, ether amines, diamines, ether diamines, ethoxylated amines, ethoxylated ether amines, or ethoxylated diamines which have found widespread prior commercial use in the manufacture of antirust and dispersant/detergent lubricant and fuel additives. These mixed borates are also derived, in part, from sulfurized alkylphenols which are being widely used in the manufacture of highly overbased calcium phenates possessing high temperature detergency and antiwear properties. Accordingly, these new compositions of matter possess a diversity of multifunctional characteristics, and are free from potentially detrimental phosphorus and metallic components.

The data detailed hereinabove confirms that the use of lubricant compositions as disclosed herein provides a significant reduction of friction coupled with oxidative stability and a substantial fuel economy benefit to internal combustion engine oils.

It is understood by those of ordinary skill in the art that the products from the preferred embodiments described herein can be effectively made and that such variations are within the scope of the specification.

What is claimed is:

1. A lubricant composition comprising a major proportion of an oil of lubricating viscosity or a grease prepared therefrom and a minor effective proportion of a multifunctional additive having friction reducing, antioxidation and corrosion inhibition characteristics consisting of an amine or alkoxylated amine sulfurized phenol borate or mixtures thereof wherein said amine is selected from the group consisting of a hydrocarbyl monoamine or diamine, a hydrocarbyloxy hydrocarbylene monoamine or diamine, a hydrocarbyl alkoxylated monoamine or diamine, a hydrocarbyloxy hydrocarbylene alkoxylated monoamine or diamine and wherein hydrocarbyl comprises a member selected from the group consisting of alkyl, alkylene, cycloalkyl, aryl and alkaryl or mixtures thereof.

2. The composition of claim 1 wherein the amines have the following general structures:

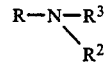

where R is from about $C_6$ to about $C_{30}$ hydrocarbyl or hydrocarbyloxy, $R^2$ and $R^3$ each separately are, H, $(R^1)_xH$, R or

$R^1$ is $C_2$ or $C_3$ hydrocarbyloxy, $R^4$ is $C_2$ or $C_3$ hydrocarbyl, $R^5$ and $R^6$ each separately are H or $(R^1)_xH$ and wherein x is from 1 to about 10.

3. The composition of claim 1 wherein said additive is bis(2-hydroxyethyl)cocoamine-dodecylphenol sulfide borate.

4. The composition of claim 1 wherein said additive is bis(2-hydroxyethyl)oleylamine-dodecylphenol sulfide borate.

5. The composition of claim 1 wherein said additive is N-oleyl-1,3-propylenediamine-dodecylphenol sulfude borate.

6. The composition of claim 1 wherein said additive is oleylamine-dodecylphenol sulfide borate.

7. The composition of claim 1 wherein said oil of lubricating viscosity is selected from the group consisting of mineral oils or fractions thereof, synthetic oils or mixtures of mineral and synthetic oils.

8. The composition of claim 1 wherein said oil is a mineral oil.

9. The composition of claim 3 wherein said oil is a mineral oil.

10. The composition of claim 4 wherein said oil is a mineral oil.

11. The composition of claim 5 wherein said oil is a mineral oil.

12. The composition of claim 6 wherein said oil is a mineral oil.

13. The composition of claim 1 wherein said oil is a synthetic oil.

14. The composition of claim 3 wherein said oil is a synthetic oil.

15. The composition of claim 4 wherein said oil is a synthetic oil.

16. The composition of claim 5 wherein said oil is a synthetic oil.

17. The composition of claim 6 wherein said oil is a synthetic oil.

18. The composition of claim 1 wherein said major proportion is a grease.

19. The composition of claim 18 wherein said grease is a lithium hydroxylcarboxylate soap grease.

20. The composition of claim 1 containing from about 0.1 to about 10 wt. % of said additive.

21. The composition of claim 20 containing from about 2 to about 4 wt. % of said additive.

22. A multifunctional friction-reducing additive product having the following general structure:

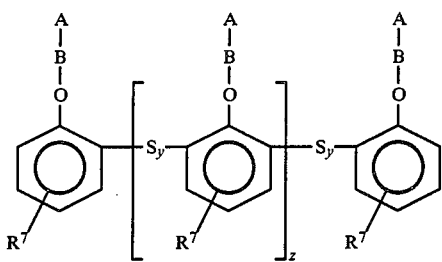

where $R^7$ is hydrogen or from about $C_3$ to about $C_{30}$ hydrocarbyl, Y is from 1 to about 4, Z is 0 to about 4, and A is one or more amine of the below generalized amine structures or mixtures thereof:

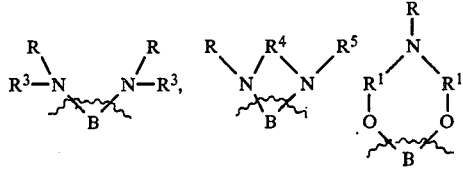

wherein R is from $C_6$ to about $C_{30}$ hydrocarbyl or hydrocarbyloxy, $R^3$ is H, $(R^1)_xH$, R or

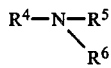

wherein $R^1$ is $C_2$ to $C_3$ hydrocarbyloxy, $R^4$ is $C_2$ to $C_3$ hydrocarbyl and $R^5$ and $R^6$ are each separately H or $(R^1)_xH$, and wherein x is from 1 to about 10.

23. A lubricant composition comprising a major proportion of an oil of lubricating viscosity or grease prepared therefrom and a minor effective proportion of a multifunctional additive having friction reducing, antioxidation and corrosion inhibiting characteristics consisting of an amine or alkoxylated amine sulfurized hydrocarbyl phenol borate or mixtures thereof derived from amines having the following general structures:

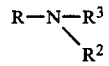

where R is from about $C_6$ to about $C_{30}$ hydrocarbyl or hydrocarbyloxy, $R^2$ and $R^3$ each separately are H, $(R^1)_xH$, R or

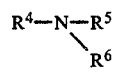

wherein $R^1$ is $C_2$ or $C_3$ hydrocarbyloxy, $R^4$ is $C_2$ or $C_3$ hydrocarbyl, $R^5$ and $R^6$ each separately are H or $(R^1)_xH$ and wherein x is from 1 to about 10; sulfurized hydrocarbyl phenols having the following generalized structure:

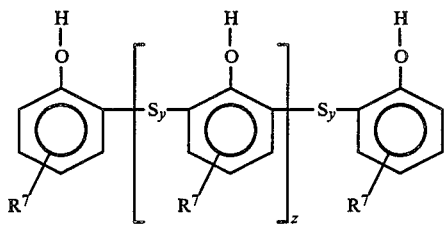

where $R^7$ is H or from about $C_3$ to about $C_{30}$ hydrocarbyl, Y is from 1 to about 4 and Z is from 0 to about 4; and a boronating agent.

24. The composition of claim 23 wherein the boronating agent is selected from boric acid or a trihydrocarbyl borate.

* * * * *

UNITED STATES PATENT AND TRADEMARK OFFICE
CERTIFICATE OF CORRECTION

PATENT NO. : 4,587,026

DATED : May 6, 1986

INVENTOR(S) : Andrew G. Horodysky

It is certified that error appears in the above-identified patent and that said Letters Patent is hereby corrected as shown below:

Column 7, line 44, "Bis(2-hydroxyyethyl)" should read
--Bis(2-hydroxyethyl)--.

Column 7, line 48, "bozate" should be --borate--.

Column 7, line 49, "dodecylophenol" should read --dodecylphenol--.

Column 9, line 10, "Bis(2-hydroxyetyl)" should read --Bis(2-hydroxyethyl)--

Signed and Sealed this

Eighteenth Day of November, 1986

*Attest:*

DONALD J. QUIGG

*Attesting Officer*      *Commissioner of Patents and Trademarks*